(12) United States Patent
Bracken et al.

(10) Patent No.: US 6,716,200 B2
(45) Date of Patent: Apr. 6, 2004

(54) ANTIMICROBIAL URINE COLLECTION SYSTEM AND METHODS OF MANUFACTURING THE SAME

(75) Inventors: Ronald L. Bracken, Conyers, GA (US); James M. Lambert, Conyers, GA (US)

(73) Assignee: C.R. Bard, Inc., Covington, GA (US)

( * ) Notice: Subject to any disclaimer, the term of this patent is extended or adjusted under 35 U.S.C. 154(b) by 0 days.

(21) Appl. No.: 10/052,766

(22) Filed: Jan. 18, 2002

(65) Prior Publication Data

US 2003/0139730 A1 Jul. 24, 2003

(51) Int. Cl.[7] ................................................ A61M 5/32
(52) U.S. Cl. ...................................... 604/265; 604/328
(58) Field of Search ................................ 604/264, 265, 604/327, 328, 346, 347–350, 355

(56) References Cited

U.S. PATENT DOCUMENTS

| | | | |
|---|---|---|---|
| 3,598,127 A | * | 8/1971 | Wepsic ......................... 604/265 |
| 4,372,313 A | | 2/1983 | Villari et al. ................. 128/295 |
| 4,539,234 A | | 9/1985 | Sakamoto et al. ........ 427/393.5 |
| 4,563,485 A | | 1/1986 | Fox, Jr. et al. .............. 523/113 |
| 4,581,028 A | | 4/1986 | Fox, Jr. et al. .................. 623/2 |
| 4,592,920 A | * | 6/1986 | Murtfeldt ..................... 427/2.3 |
| 4,603,152 A | | 7/1986 | Laurin et al. ................ 604/265 |
| 4,623,329 A | | 11/1986 | Drobish et al. ................ 604/29 |
| 4,642,104 A | | 2/1987 | Sakamoto et al. ........... 604/264 |
| 4,675,347 A | * | 6/1987 | Mochizuki et al. .......... 523/122 |
| 4,696,329 A | | 9/1987 | Izzi ................................. 141/1 |
| 4,696,672 A | | 9/1987 | Mochizuki et al. .......... 604/128 |
| 4,723,950 A | | 2/1988 | Lee .............................. 604/322 |
| 4,917,686 A | | 4/1990 | Bayston et al. .............. 604/265 |
| 4,925,668 A | | 5/1990 | Khan et al. ................... 424/422 |
| 5,007,897 A | | 4/1991 | Kalb et al. ..................... 604/43 |
| 5,019,378 A | * | 5/1991 | Allen ........................ 514/772.4 |
| 5,098,379 A | | 3/1992 | Conway et al. ................ 604/51 |
| 5,137,671 A | | 8/1992 | Conway et al. .............. 264/130 |
| 5,176,665 A | | 1/1993 | Watanabe et al. ............ 604/317 |
| 5,217,493 A | | 6/1993 | Raad et al. ...................... 623/11 |
| 5,236,422 A | | 8/1993 | Eplett, Jr. ..................... 604/265 |
| 5,261,896 A | | 11/1993 | Conway et al. .............. 604/265 |
| 5,269,770 A | | 12/1993 | Conway et al. .............. 604/265 |
| 5,312,379 A | | 5/1994 | Rahe ............................ 604/318 |
| 5,362,754 A | | 11/1994 | Raad et al. ................... 514/566 |
| 5,482,740 A | | 1/1996 | Conway et al. .............. 427/2.28 |
| 5,492,763 A | * | 2/1996 | Barry et al. .................. 428/457 |
| 5,498,416 A | | 3/1996 | Carsenti-Etesse et al. .. 424/422 |
| 5,554,147 A | | 9/1996 | Batich et al. .............. 604/890.1 |
| 5,569,463 A | | 10/1996 | Helmus et al. .............. 424/426 |
| 5,599,321 A | | 2/1997 | Conway et al. .............. 604/265 |
| 5,607,417 A | | 3/1997 | Batich et al. .............. 604/890.1 |
| 5,624,704 A | | 4/1997 | Darouiche et al. .......... 427/2.24 |
| 5,709,672 A | | 1/1998 | Illner ............................ 604/265 |
| 5,718,624 A | | 2/1998 | Volk ............................. 452/176 |
| 5,772,640 A | | 6/1998 | Modak et al. ................ 604/265 |
| 5,820,607 A | | 10/1998 | Tcholakian et al. ......... 604/265 |
| 5,843,436 A | | 12/1998 | Loike et al. ............... 434/94.64 |
| 5,997,815 A | | 12/1999 | Anders et al. ................. 422/35 |
| 6,017,741 A | | 1/2000 | Keogh .......................... 435/174 |
| 6,022,553 A | | 2/2000 | Anders et al. ................ 424/411 |
| 6,110,483 A | | 8/2000 | Whitbourne et al. ........ 424/423 |
| 6,119,192 A | | 9/2000 | Kao et al. ..................... 710/128 |
| 6,162,487 A | | 12/2000 | Darouiche ................... 427/2.14 |
| 6,224,579 B1 | | 5/2001 | Modak et al. ................ 604/265 |
| 6,492,445 B2 | * | 12/2002 | Siddiqui et al. .............. 524/156 |

* cited by examiner

*Primary Examiner*—Weilun Lo
*Assistant Examiner*—Michael G. Bogart
(74) *Attorney, Agent, or Firm*—Stroock & Stroock & Lavan LLP

(57) ABSTRACT

An antimicrobial urine collection system comprising a urine collection bag and tubing each made from a polymer, wherein the polymer comprises therein from about 0.1 to 20 phr of an antimicrobial agent. The antimicrobial agent is preferably a phosphoric acid metal salt, preferably one in which zinc is the metal. The agent can be compounded into the polymer material for forming the system components.

21 Claims, 1 Drawing Sheet

ANTIMICROBIAL URINE COLLECTION SYSTEM AND METHODS OF MANUFACTURING THE SAME

FIELD OF THE INVENTION

The invention is directed to an antimicrobial urine collection system and methods of making the same.

BACKGROUND OF INVENTION

Urinary collection containers and/or drainage bags are generally used for collecting urine from a catheterized patient. Such systems typically comprise a catheter having tubing attached thereto that leads to a collection bag made of a polymer material such as PVC film. The collection bag generally includes a means for emptying the bag, such as a drainage tube.

Patients are generally catheterized either internally or externally. Cathertization often results in the possibility of urinary tract infections created from microorganism growth within the collection bag and its associated tubing. Recent studies have shown that hospital acquired or "nosocomial" urinary tract infections (UTI) affect about 900,000 Americans annually. J. R. Johnson, P. L. Roberts, R. J. Olsen, K. A. Moyer, and W. E. Stann, Prevention of Catheter Associated Urinary Tract Infection with a Oxide-Coated Urinary Catheter Clinical and Microbiologic Correlates, 162 Journal of Infectious Diseases, 1145–1150 (1990). Many of these UTIs are acquired in hospitals with the result that UTIs account for about 40% of all hospital acquired infections. Id. Of the UTIs acquired in hospitals, about 80% are catheter associated. Id. These hospital related UTIs were found to prolong hospital stays by an average of 2.4 to 4.5 days and increase the hospital cost by $558.00 per episode. Id. If the percent of catheter associated UTIs could be reduced to 0, the annual saving in hospital cost alone could be reduced by $401,760,000.00.

A source of the catheter related UTIs is suspected to be bacteria progressing from the patient's meatus through the peri-urethral space into the bladder. One known method for attempting to prevent bacterial caused UTIs is disclosed in U.S. Pat. No. 4,773,901 to Norton, the contents of which are incorporated herein by reference. In the Norton patent, the urinary catheter is coated with silver oxide to kill bacteria which may find its way down the patient's periurethral space.

In the field of urinary catheters, there is a body of art pertaining to preventing pathogens from migrating from a urine collection bag up through a catheter and into the urethra. Illustrative of this urinary catheter art are U.S. Pat. Nos. 4,529,398 by Wong; 4,661,100 by Rechsteiner; 5,267,989 by Moyet-Ortiz; 4,863,445 by Mayhan; 4,417,892 by Meisch; and 4,372,313 by Villari. The contents of each of these patents is incorporated hereby by reference.

A typical approach to preventing urinary tract infections in the urinary catheter prior art is to include a sterilizing agent in the catheter or in the collection bag so that pathogens cannot migrate up the catheter. In the Wong patent, a dispensing device having a polymer with a chemoprophylactic agent is placed within the collection bag. The dispensing device begins sterilizing liquid in the collection bag immediately upon contact, and the device is designed such that the sterilizing properties continue for an extended period of time. However, in dialysis collection bags it is desirable that the sterilization of the liquid not be commenced immediately upon contact with the dialysis collection bag, and in dialysis collection bags it is not necessary that the sterilization be contained for an extended period of time because the bag is filled in a very short period of time rather than over a period of many hours.

The Rechsteiner patent discloses a system with a urine collection bag having a fragile resinous material inside which is broken to release a sterilizing or diagnostic agent. The Rechsteiner patent is like the Wong patent in that it is designed for urinary catheter applications in which the collected urine must be sterilized immediately upon contact and over an extended period of time to prevent pathogen migration into the patient. The Mayhan patent is similar to the Rechsteiner patent, except that the resinous sterilizing agent is replaced with a slow-dissolving tablet. The Moyet-Ortiz patent discloses an antiseptic absorbent pad in a urine collection device; the Meisch patent discloses an outlet tube to a urine collection bag which is treated with a sterilizing agent to prevent pathogen colonization; the Villari patent discloses a urine collection bag with a tubular portion having a device for retaining an antimicrobial agent. These known systems can be overly complicated or otherwise less than satisfactory to construct or use.

There are many drugs, compounds, solutions, and/or materials that show antimicrobial properties, some of which are silver salts, penicillin, sulfa drugs, chlorhexidine and many others known in the art. However, many of the known antimicrobials are plagued with being heat sensitive and degrade at temperatures that are reasonable and customary for injection molding or extrusion of articles, in particular, urine collection bags. Similarly, some known antimicrobials are plagued with discoloring when exposed to light or heat, some are opaque which would render articles that need to be transparent opaque or hazy, some have odors that are noticeable to users, and some are water soluble, which in a urine collection device would leach or dissolve into the urine which would lower the amount available in the compounded article and potentially weaken the article or cause pinholes in the article.

Accordingly, there is a need for an effective antimicrobial urine collection system that provides protection from urinary tract infections for catheterized patients. It is also desirable to provide an improved method of making urine collection systems, such as by reducing the number of manufacturing steps or by making existing manufacturing systems compatible for manufacturing an antimicrobial article, or improving the final product.

SUMMARY OF THE INVENTION

The present invention is directed at an antimicrobial urine collection system and methods of making the same. In particular, the present invention is directed at an antimicrobial urine collection system comprising a catheter (such as a silicone or natural or synthetic rubber catheter), a polymer urine collection bag (such as a PVC film bag), and associated polymer or synthetic rubber tubing (such as PVC drainage and outlet tubing) that are rendered antimicrobially effective by incorporating therein an effective amount of an antimicrobial agent. The present invention is also directed at methods of making such antimicrobial urine collection systems.

A urine collection system in accordance with the invention generally includes a catheter, a urine collection bag, advantageously made from polymer film, and associated tubing. The catheter can be made of silicone or natural or synthetic rubber, the urine collection bag can be made of various polymers, such as polyvinyl chloride (PVC or vinyl), polyethylene, polypropylene, ethylene vinyl acetate, metallocene catalyzed polyethylene, or blends thereof, and the associated outlet and drainage tubing is typically made of PVC or synthetic rubber. The present invention is directed at incorporating an antimicrobially effective amount of an antimicrobial agent into the catheter, PVC film and tubing, not merely coating the outside of the polymer materials.

In one aspect of the present invention, the antimicrobial agent is a phosphoric acid metal salt, and the polymer is a PVC film and tubing. Each can advantageously comprise, by parts per hundred resin (phr), from about 0.1 to 20 phr of the antimicrobial agent, more preferably 0.5 to 7.5 phr and most preferably about 3 phr. In one embodiment of the present invention, the phosphoric acid metal salt is ADK Royalguard® BS-340 which is a commercially available stabilizing agent from Amfine Chemical Corporation of Allendale, N.J., which has been found to provide antimicrobial properties. Systems in accordance with the present invention can be made to retain the antimicrobial agent in a sustained and controlled manner.

In another aspect of the present invention, the antimicrobial agent comprises both an antimicrobial element and an additional stabilizing element. In a preferred embodiment, the antimicrobial element of the antimicrobial/stabilizing agent ("the A/S agent") is a phosphoric acid metal salt, particularly one in which zinc is the metal, and the further stabilizing element can be zinc stearate. Conventional stabilizers include calcium stearate, mixed-metal-salt blends, organotin compounds and lead compounds. Antimony mercaptides are also used to a lesser extent. Typical mixed-metal heat stabilizers are barium and cadmium (Ba/Cd) metal salts (soaps). Individual organic heat stabilizers usually consists of methyltin, butyltin, and octyltin mercaptides, maleates and carboylates. It has been found that the bag and tube formation process can degrade the antimicrobial properties of the phosphoric acid metal salt. Thus, the addition of stabilizers can help maintain suitable antimicrobial effectiveness.

In one embodiment of the present invention, the PVC film and tubing each comprise, by parts per hundred resin (phr), from about 0.1 to 20 phr of the combined A/S agent, more preferably 0.5 to 7.5 phr and most preferably about 4.5 phr. In a preferred embodiment of the present invention, the A/S agent is ADK Royalguard® BS-340. ADK Royalguard® BC-200, BC-250 or BC-310 can also be used. Each are commercially available from Amfine Chemical Corporation.

In one aspect of the present invention, the A/S agent comprises from about 0.05 to 15 phr (parts per hundred resin) of a phosphoric acid metal salt, more preferably 0.3 to 5 phr and most preferably about 3 phr. Also, in a preferred embodiment, the A/S agent comprises from about 0.1 to 5 phr (parts per hundred resin) of a stabilizer, more preferably from about 0.2 to 2.5 phr and most preferably about 1.5 phr of a stabilizer. In a preferred embodiment, 0.5 to 0.75% of the A/S agent should be the antimicrobial agent.

Other objects and features of the present invention will become apparent from the following detailed description, considered in conjunction with the accompanying drawing figures. It is to be understood, however, that the drawings are designed solely for the purpose of illustration and not as a definition of the limits of the invention, for which reference should be made to the appended claims.

BRIEF DESCRIPTION OF THE DRAWINGS

In the drawing figures, which are merely illustrative.

DETAILED DESCRIPTION OF THE PREFERRED EMBODIMENTS

Figure 1:
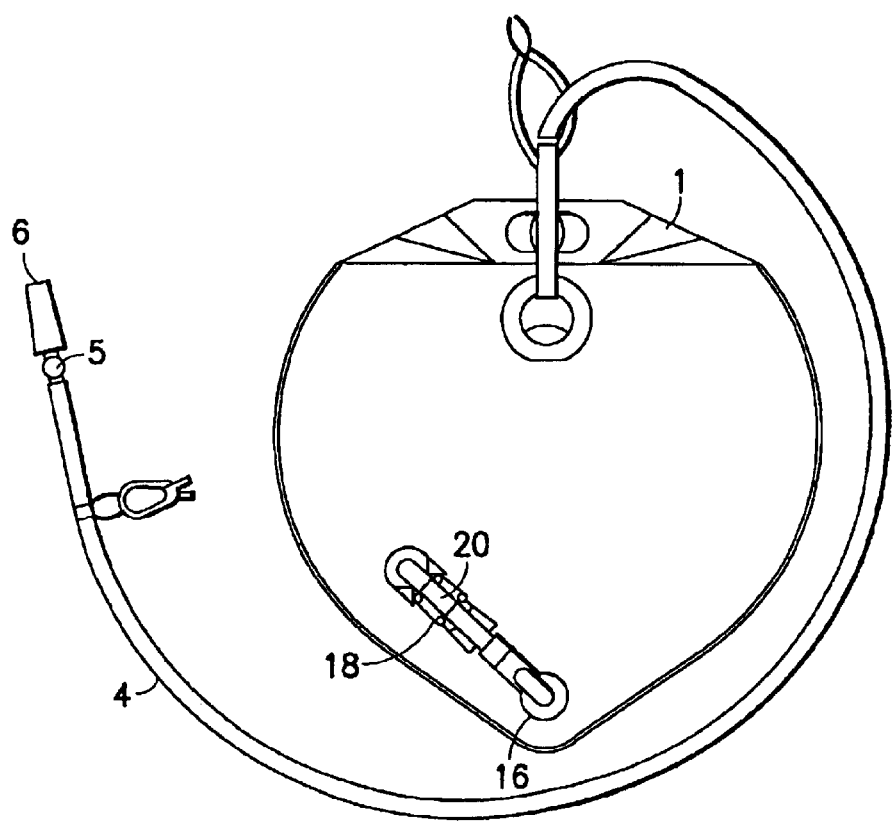
FIG. 1 is a schematic view of a typical urine collection system in accordance with preferred embodiments of the invention.

The present invention is directed at an antimicrobial urine collection system and methods of making the same. Urine collection systems in accordance with the invention generally comprise a catheter, a urine collection bag and associated tubing. The catheter can generally be made of silicone or natural or synthetic rubber, with silicone and natural rubber being the preferred materials. The urine collection bag can be made of various polymers, such as polyvinyl chloride (PVC or vinyl), polyethylene, polypropylene, ethylene vinyl acetate, metallocene catalyzed polyethylene, or blends thereof, and the associated outlet and drainage tubing is typically made of PVC or synthetic rubber, with PVC being the preferred material for the collection bag and tubing.

A typical urine collection system for use with catheterized patients is depicted in FIG. 1. The system generally includes a urine collection bag, generally indicated as 1, a drainage tube, generally indicated as 4, which is connected to a sampling port 5 and a catheter connector 6 for connecting tube 4 to a catheter (not shown), such as a Foley catheter. A typical collection bag 1 also includes an outlet tube port 16 which has an outlet tube/connector mechanism 18 for emptying collection bag 1 through an outlet tube 20.

As one of skill in the art will recognize, in general terms, a catheter, such as a Foley catheter, is inserted into the bladder of a patient. The catheter is then connected to connector 6 of the urine collection system. The urine flows from the patient into the tubing 4 and then flows into collection bag 1. As one of skill in the art will recognize, to empty collection bag 1, a technician generally disengages outlet tube/connector mechanism 18 which swings downward, thereby permitting the urine to flow out of collection bag 1 through outlet tube 20. As one of skill in the art will also recognize, sampling port 5 can be used by a technician in order to collect a sample of the urine within the collection bag in an antiseptic manner. In general, a technician would simply insert a plastic or metal cannula into the sampling port to draw a sample of the urine that is within tube 4. Because measuring urine bacterial levels often occurs from urine collected in the bag, it can be an important aspect of the invention to provide the antimicrobial material in a manner so as to prevent migration of bacteria to the patient, but not to kill the bacteria in the urine in the bag, or not to kill the bacteria so fast that it cannot be collected and tested to provide important medical data.

A new antimicrobial and class of antimicrobials have been identified for medical applications, which can be compounded into the resin and extruded into the film used in manufacturing urine collection drainage bags and associated tubing. This can improve the manufacturing process as well as antimicrobial effectiveness. With the choice of several antimicrobials within this class of compounds and with the ability to incorporate one or more of the antimicrobials at different and varying levels and incorporate them at vendors sites when the article is being fabricated, a system can be tailor-made that has optimized antimicrobial properties in the drainage tubing, bag itself, outlet tubing, connectors, etc.

A preferred antimicrobial material for use in the urine collection system of the present invention is organic acid metal salts, such as salts comprising phosphoric acid esters and zinc metal, particularly materials that can provide a stabilizing effect to polymers, and, in particular, a heat stabilizing effect to PVC and other polymer materials for use in the urine collection system of the present invention.

Preferably, the antimicrobial material is ADK Royalguard® BS-340, which is a commercially available organic acid metal salt stabilizer from Amfine Chemical Corporation.

ADK Royalguard® BS-340 is a zinc phosphoric acid ester which provides several benefits over silver based antimicrobial compounds. This, and compounds like it, are similar to silver compounds in their antimicrobial properties, but are much less likely to discolor under heat and light and provide other benefits. They can also be effective against a wide range of microorganisms.

As can be appreciated, there are many antimicrobial compounds known that may not be able to withstand the heat involved in injection molding or extrusion or heat welding. There are also many compounds that may adversely affect the desirable properties of the articles such as clarity, strength, bond ability, etc. There are also many compounds that may not be effective against a preponderance of microorganisms. The phosphoric acid metal salt of the present invention, and most preferably ADK Royalguard® BS-340, appears to have the most desirable balance of beneficial properties with little or none of the undesirable properties.

It is also anticipated that ADK Royalguard® 13S-340 has several compounds that are related but not the same chemically and that there are other compounds that are similar or have similar desirable properties and these could be used singly or in conjunction with others in the same or other articles. It is also appreciated that the ADK Royalguard® BS-340 is low in odor and is substantially insoluble in water so that when in contact with urine, it will not leach out and become unusable or leave voids in the article.

The uniqueness of ADK Royalguard® BS-340, and other compounds like it, are that they can be compounded in the various materials used to make the components of the urine collection system, e.g., natural or synthetic rubber, silicone, various polymers, such as PVC or vinyl, polyethylene, polypropylene, ethylene vinyl acetate, metallocene catalyzed polyethylene, or blends thereof, etc., before the article is molded or extruded, and the material will not significantly affect the desirable properties of the article, i.e., drainage tubing would be essentially clear and not discolored, the tubing can still be solvent bonded, the film can still be RF or heat welded, it would not be toxic, significant amounts would not leach out, and the article or product would remain antimicrobial for extended periods of time.

The antimicrobial substance could be incorporated into all or some of the components used to fashion a urine collection bag. Such a bag would minimize microorganism populations, therefore creating less potential for urinary tract infections. The antimicrobial urine bag of the present invention provides protection against microorganisms that may be flushed from the catheter. Systems in accordance with this invention can help minimize bacterial adherence and resist migration of external bacteria from external sources into the patient. Examples of such microorganisms include, but are not limited to, *Candida tropicalis, Citrobacter diversus, Enterobacter cloacae, Enterococcusfaecalis, Escherichia coli, Klebsiella pneumoniae, Proteus mirabilis, Pseudomonas aeruginosa, Staphylococcus saprophyticus, Enterococcus durans*, and many others. The benefits of including an antimicrobial agent into the collection bag additionally include, but are not limited to, protection from reflux and inhibiting and/or restricting bacterial growth. That is, the antimicrobial agent can provide protection from reflux of urine which may contain microorganisms from contaminating or recontaminating the bladder, i.e., the urine may still reflux but it will now be urine that has contacted the antimicrobial and should therefore be substantially bacteria free. Another aspect is that the antimicrobial being compounded into the various parts of the bag, rather than as an additive or pellet to the inside of the bag, it will not plug up any of the tubing nor be washed out of the bag as it dissolves. Also it can inhibit and/or restrict bacterial growth both on the inside and outside of the bag.

The urine collection bag and associated drainage and outlet tubing of the present invention is preferably made from a polyvinyl chloride. Concentrations of the antimicrobial agent can range from, by parts per hundred resin (phr), from about 0.1 to 20 phr of the antimicrobial agent, more preferably 0.5 to 7.5 phr and most preferably about 3 phr.

The antimicrobial materials described herein could also be useful for any product in which microorganisms need to be killed or reduced, such as suction canisters that hold body fluids, wound drainage articles, plastic forceps, injection or molded connectors or fitments or other attachments to urine collection devices, and other such devices or products. The present invention is also not limited to injection or blow molded articles, as it could also be used in extruded articles, such as urine drainage tubes, suction tubing, extension tubing, etc. Other articles where it might be particularly useful is in extruded or calendared film such as that which might be used in making urine collection bags. The present invention is also not limited to injection or blow molded or extruded or calendared articles, solvent cast articles or films could be made, such as films or inserts as well as rubber type articles, such as outlet tubes, that are coagulated emulsions or suspensions. It is also conceivable that these types of compounds could be used to cast or co-extrude thin or thick films on articles, tubing, or films.

It is therefore conceivable that a urine collection device, including a connector, drainage tubing, urine collection meter or dome, collection bay, outlet port, outlet tube, and any attachments/fitments (e.g., tube holder, hanger, vent, string, etc.) could have these materials incorporated into it at the same or different amounts depending on the needs and have the total system show activity against microorganisms.

It is also anticipated that other medical articles could also be rendered antimicrobial or resistant to microorganisms, some such articles are thermoformed trays for packaging, inks used for printing on said articles, gloves, sterile water or lubrication used with the products, drapes and CSR wraps and many others.

It is also appreciated that these types of compounds are powders which can be easily handled and mixed into resins before forming into useful articles, that these types of agents have low toxicity to humans and animals such that workers handling the compound will not be harmed and upon disposal of the article the agent will not leak or harm animals and marine life in the environment. It is also appreciated that these agents are heat stable and can endure injection molding and extrusion temperatures in excess of 250–350° F., and even over 500° F.

This disclosed class of antimicrobials are heat stable and will not substantially degrade, they will not discolor or discolor to a very low extent, they leave the article they are incorporated into transparent or much less hazy than other antimicrobials, they do not have an odor associated with them, they have little or no water solubility, thus there may always be antimicrobial agent available as a function of time. The disclosed class of antimicrobials have a wide spectrum of activity (against gram positive, gram negative and yeasts), they produce little or no discoloration, when exposed to heat, light, radiation or moisture, they are inexpensive and easy to manufacture.

The efficacy of the system of the present invention was evaluated in studies and the following examples are illustrative of the tests that were undertaken. The following examples are intended to further illustrate the present invention, but the invention is not intended to be limited thereto.

A method of manufacturing a urine collection system in accordance with the present invention is as follows:

EXAMPLE 1

Making a Urine Collection System

A. Compound the antimicrobial agent into the PVC resin.

Royalguard® BS-340 is blended into the PVC resin pellets at a concentration of 4.5 phr. One skilled in the art can recognize that this be done via tumbling the powder with the pellets, coating the outside of the pellets, passing the resin and powder through an extruder and forming new pellets containing Royalguard®, or compounding in the powder with additives (i.e. colorants, stabilizers, inhibitors). This is one place where a separate antimicrobial manufacturing step can be eliminated since a colorant, stabilizer, or other additive is typically added at this point.

B. Extrude tubing and calendar film out of the PVC resin. Typical extrusion temperatures (and typical calendaring temps) are 330–345° F., which is at or about the melt temperature of the resin. The Royalguard® containing pellets are placed into an extruder. Generally the pellets are taken from room temperature through a ramp up temperature of room temp. to 200–250° F. in zone 1 to 250–300° F. in zone 2 to 300–350° F. in zone 3 and then if there are other zones in the extruder they are kept at 300–350° F. The extruder is used to form the drainage tubing by extruding molten PVC through a crosshead containing a pin and die to form the tube.

Additional pellets are taken to a calendaring operation where film is made by passing the pellets between two heated rolls and pressed into a thin film. The calendaring rolls are generally heated to a sufficient temperature so as to achieve melting of the pellets, e.g., 330–345° F.

C. RF weld/seal film into drainage bag configuration.

The film is now ready for assembly into a bag. The film is RF welded into a bag using a, e.g., Thermotron RF welder at 1–4 kilowatts. The bag has fitments attached, such as, the outlet tube fitment, drainage tube fitment, and a vent. These fitments can be welded at the same time the bag is formed.

D. Connect drainage tubing to bag.

The drainage tubing can be connected to the bag by applying a small amount of cyclohexanone to the tube. The tube is then placed into the drainage tube fitment which was previously RF welded to the bag.

E. Connect tubing to catheter connector/sampling port. Catheter connector could be molded from an antimicrobial-containing plastic.

The end of the drainage tubing opposite the bag is connected to a sampling port fitment. The sample port fitment is connected to the catheter at the end opposite the drainage tubing using cyclohexanone.

F. Affix an antimicrobial outlet tube to bag. Again, the outlet tube and sampling port can contain this or other members of the family of antimicrobials.

The outlet tube is applied to the bag by applying a small amount of cyclohexanone to the outlet tube. The outlet tube is placed over the outlet tube fitment previously RF welded to the bag.

G. Package the antimicrobial system for sale.

The entire completed system is then placed in a package and sterilized via ethylene oxide sterilization.

The efficacy of the system of the present invention was evaluated in studies and the following examples are illustrative of the tests that were undertaken. The following examples are intended to further illustrate the present invention, but the invention is not intended to be limited thereto.

Testing of product manufactured per Example 1

| Sample ID | Elongation at Break % | Tensile Strength at Break | Zone of Inhibition (ZOI) Gram Positive | Gram Negative | Yeast |
|---|---|---|---|---|---|
| PVC Inlet Tube (4.5 phr of BS-340) | N/A | 82.9 lbs. | Yes | Yes | Yes |
| PVC Inlet Tube (no BS-340) | N/A | 84.6 | No | No | No |
| PVC Film (4.5 phr BS-340) | 220 | 7.7 lbs (2800 psi) | Yes | Yes | Yes |
| PVC Film (No BS-340) | 225 | 7.5 lbs (2700 psi) | No | No | No |
| Synthetic Rubber Outlet Tube (4.5 phr of BS-340) | N/A | 47.7 lbs | Yes | Yes | Yes |
| Synthetic Rubber Outlet Tube (No BS-340) | N/A | 30.7 lbs | No | No | No |

The above table indicates that the addition of Royalguard ® BS-340 does not detrimentally affect the overall physical properties of the components, and, antimicrobial activity was observed. As one of skill in the art will recognize, the term ZOI denotes an antimicrobial effect in the product.

EXAMPLE 2

Solvent Casting of Films

The following procedure was performed:

A. Make a solution with 24.25 grams of PVC and 275 grams of tetrahydrofuran (THF).

B. Place on roller until PVC totally dissolves.

C. Make the following Royalguard® BC-250 solution: 0.75 grams of Royalguard® BC-250 is added to 25 grams of ethanol.

Add ethanol solution containing Royalguard® BC-250 to the PVC solution.

Mix on roller until ethanol solution is completely incorporated.

Take 80 ml of BC-250/PVC solution and transfer to spincaster. Allow to spin for one hour.

Samples were allowed to dry overnight.

EXAMPLE 3

Compounding of Royalguard® BC-310 into Silicone Elastomer

Royalguard® BC-310 was blended with a 1000 centistokes polydimethylsiloxane fluid. The blending ratio was 1:1, weight to weight.

Took a high consistency rubber (HCRA-70, Rhodia Silicones Ventura, Calif. 93001) and placed 908.35 g Part B on a two roll rubber mill and freshened by passing through the nip several times. Part B was removed from the rolls and 908.46 g Part A was placed on the mill and freshened by passing through the nip several times.

After part A was freshened 107.14 g of Royalguard®/silicone fluid was added to part A. Several passes were made through the nip to ensure mixing.

Once the powder was mixed into Part A, Part B was then combined with Part A on the mill. The material was crosscut, cigar rolled, and passed through the nips approximately 7 times.

The compounded elastomer was then used to mold test plaques using a heated press. The molding conditions were 240° F. for 10 minutes. Plaque mold cavity was 0.045 inches deep.

The material was tested for tensile strength, elongation, and antimicrobial activity using zone of inhibition.

Results:

| Sample ID | Elongation at Break (%) | Tensile Strength at Break | Zone of Inhibition (ZOI) | | |
|---|---|---|---|---|---|
| | | | Gram Positive | Gram Negative | Yeast |
| 70 durometer silicone with BC-310 | 475 | 1057 | Yes | Yes | Yes |
| 70 durometer silicone w/o Royalguard | 550 typical | 1300 typical | No | No | No |

Thus, while there have been shown and described and pointed out fundamental novel features of the invention as applied to preferred embodiments thereof, it will be understood that various omissions and substitutions and changes in the form and details of the disclosed invention may be made by those skilled in the art without departing from the spirit of the invention. It is the intention, therefore, to be limited only as indicated by the scope of the claims appended hereto.

What is claimed is:

1. An antimicrobial urine collection system comprising a urine collection bag and tubing coupled to the bag and constructed to transport urine to the bag, the bag and tubing each made from a polymer, wherein said polymer of the bag or tubing is substantially clear and comprises therein from about 0.1 to 20 phr of an antimicrobial agent, said agent substantially resistant to heat up to at least the melting point of said polymer, substantially uniformly distributed therein, said antimicrobial agent not substantially affecting the clarity of the polymer, and exhibiting an antimicrobial effect.

2. The urine collection system according to claim 1, wherein said polymer comprises therein from about 0.5 to 75 phr of an antimicrobial agent.

3. The urine collection system according to claim 1, wherein said polymer comprises therein from about 4.5 phr of an antimicrobial agent.

4. The urine collection system according to claim 1, wherein said polymer is selected from the group of polymers consisting of polyethylene, polypropylene, ethylene vinyl acetate, metallocene catalyzed polyethylene, or blends thereof.

5. The urine collection system according to claim 1, wherein said polymer is polyvinyl chloride.

6. The urine collection system according to claim 1, wherein said polymer of said collection bag comprises from about 0.1 to 20 phr of an antimicrobial agent.

7. The urine collection system according to claim 1, wherein said polymer of said tubing comprises from about 0.1 to 20 phr of an antimicrobial agent.

8. The urine collection system according to claim 1, wherein said polymer of said tubing and said polymer of said collection bag each comprise from about 0.1 to 20 phr of an antimicrobial agent.

9. An antimicrobial mine collection system comprising a urine collection bag and tubing coupled to the bag and constructed to transport urine to the bag, the bag and tubing each made from a polymer, wherein said polymer of said tubing and said collection bag collection bag are each polyvinyl chloride comprising from about 0.1 to 20 phr of an antimicrobial agent that is substantially uniformly distributed therein, said antimicrobial agent not substantially affecting the clarity of the polymer, and exhibiting an antimicrobial effect.

10. The urine collection system according to claim 1, wherein said antimicrobial agent is an organic acid metal salt.

11. An antimicrobial urine collection system comprising a urine collection bag and tubing coupled to the bag and constructed to transport urine to the bag, the bag and tubing each made from a polymer, wherein said polymer of the bag or tubing comprises therein from about 0.1 to 20 phr of an antimicrobial agent that is substantially uniformly distributed therein, wherein said antimicrobial agent is an organic acid metal salt comprising phosphoric acid esters and zinc metal, said antimicrobial agent not substantially affecting the clarity of the polymer, and exhibiting an antimicrobial effect.

12. An antimicrobial urine collection system comprising a urine collection bag and tubing coupled to the bag and constructed to transport urine to the bag, the bag and tubing each made from a polymer, wherein said polymer of the bag or tubing comprises therein from about 0.1 to 20 phr of an antimicrobial agent that is substantially uniformly distributed therein, wherein said antimicrobial agent is an organic acid metal salt comprising from about 0.3 to 5 phr of a phosphoric acid metal salt and in addition, from about 0.2 to 2.5 phr of a stabilizer, said antimicrobial agent not substantially affecting the clarity of the polymer, and exhibiting an antimicrobial effect.

13. An antimicrobial urine collection system comprising a urine collection bag and tubing coupled to the bag and constructed to transport urine to the bag, the bag and tubing each made from a polymer, wherein said polymer of the bag or tubing comprises therein from about 0.1 to 20 phr of an antimicrobial agent that is substantially uniformly distributed therein, wherein said antimicrobial agent comprises from about 0.05 to 15 phr of a phosphoric acid metal salt and in addition, from about 0.1 to 5 phr of a stabilizer, said antimicrobial agent not substantially affecting the clarity of the polymer, and exhibiting an antimicrobial effect.

14. An antimicrobial urine collection system comprising a urine collection bag and tubing coupled to the bag and constructed to transport urine to the bag, the bag and tubing each made from a polymer, wherein said polymer of the bag or tubing comprises therein from about 0.1 to 20 phr of an antimicrobial agent that is substantially uniformly distributed therein, wherein said antimicrobial agent comprises from about 0.3 to 5 phr of a phosphoric acid metal salt and from about 0.2 to 2.5 phr of a stabilizer, said antimicrobial agent not substantially affecting the clarity of the polymer, and exhibiting an antimicrobial effect.

15. An antimicrobial urine collection system comprising a urine collection bag and tubing coupled to the bag and constructed to transport urine to the bag, the bag and tubing each made from a polymer, wherein said polymer of the bag or tubing comprises therein from about 0.1 to 20 phr of an antimicrobial agent that is substantially uniformly distributed therein, wherein said antimicrobial agent comprises from about 3 phr of a phosphoric acid metal salt and from about 1.5 phr of a stabilizer, said antimicrobial agent not substantially affecting the clarity of the polymer, and exhibiting an antimicrobial effect.

16. An antimicrobial urine collection system comprising a catheter joined to tubing and comprising a rubber material, wherein said rubber material comprises therein from about 0.1 to 20 phr of an antimicrobial agent wherein said antimicrobial agent is an organic acid metal salt is comprising phosphoric acid esters and zinc metal.

17. An antimicrobial urine collection system comprising a urine collection bag and tubing coupled to the bag and constructed to transport urine to the bag, the bag and tubing each made from a polymer, wherein said polymer of the bag or tubing comprises therein from about 0.1 to 20 phr of an organic acid metal salt substantially uniformly distributed therein, said organic acid metal salt exhibiting an antimicrobial effect.

18. The urine collection system according to claim 17, wherein said bag or tubing exhibit an effective gram positive, grain negative and yeast zone of inhibition.

19. The urine collection system according to claim 17, further comprising a catheter, said catheter, collection bag and tubing each manufactured in such a way so as to release said antimicrobial agent in a sustained and controlled manner.

20. A method for manufacturing antimicrobial PVC tubing comprising the steps of: compounding an antimicrobial agent comprising phosphoric acid esters and zinc metal into PVC resin pellets at an effective concentration to provide an antimicrobial effect in the tubing; placing said pellets into an extruder; and extruding said pellets through said extruder to form a tube having antimicrobial effectiveness.

21. A method for manufacturing antimicrobial PVC film for use as a urine collection bag comprising the steps of: compounding an antimicrobial agent comprising phosphoric acid esters and zinc metal into PVC resin pellets at an effective concentration to provide an antimicrobial effect in the film; placing said pellets into a calendar; and calendaring said pellets into a thin film to having antimicrobial effectiveness.

* * * * *